United States Patent [19]
Fifield

[11] 4,029,099
[45] June 14, 1977

[54] URINE DRAINAGE APPARATUS

[76] Inventor: Loretta Alice Fifield, 609 Schwab Road, Hatfield, Pa. 19440

[22] Filed: Dec. 4, 1975

[21] Appl. No.: 637,538

[52] U.S. Cl. .................... 128/295; 128/349 R
[51] Int. Cl.² ............................ A61F 5/44
[58] Field of Search ............ 128/275–278, 128/295, 348–351; 15/315; 285/226, 299, 260

[56] References Cited
UNITED STATES PATENTS

| | | | |
|---|---|---|---|
| 3,261,107 | 7/1966 | Ponczek et al. | 15/315 X |
| 3,537,457 | 11/1970 | Heimlich | 128/276 |
| 3,721,243 | 3/1973 | Hesterman et al. | 128/295 |
| 3,742,953 | 7/1973 | Lee | 128/295 |
| 3,832,999 | 9/1974 | Crilly | 128/275 |
| 3,894,540 | 7/1975 | Bonner | 128/349 R |

*Primary Examiner*—Dalton L. Truluck

[57] ABSTRACT

The fluid conducting tube leading from a catheter to a container is formed with a section of bellows-like or accordion-like construction so that when it is expanded the tube is long and when it is collapsed the tube is short. An engaging member at each end of the section can be brought together and interlocked to hold the section in collapsed formation.

4 Claims, 7 Drawing Figures

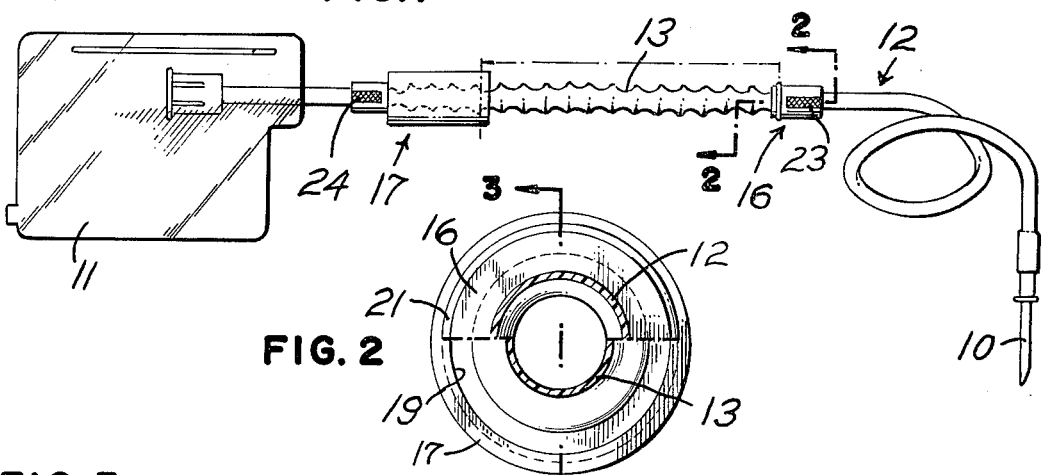
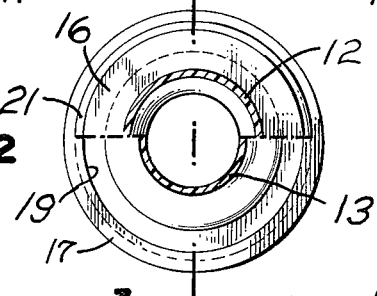
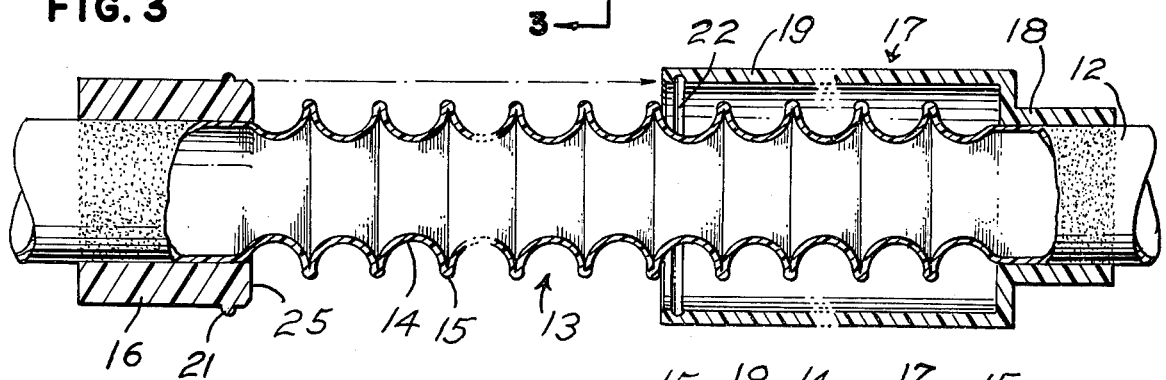
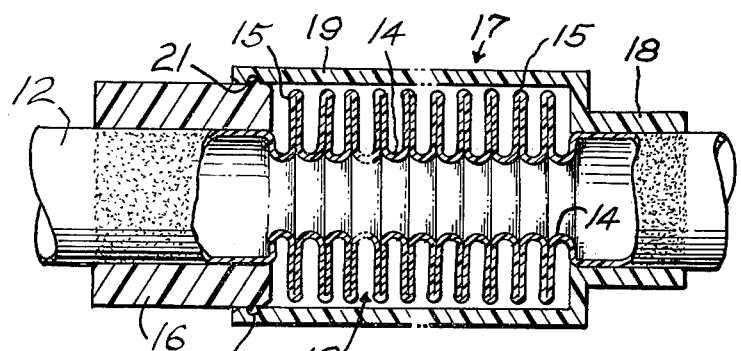
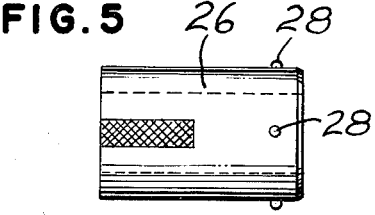
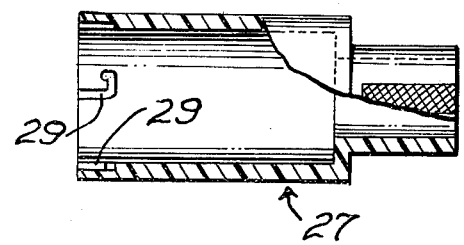
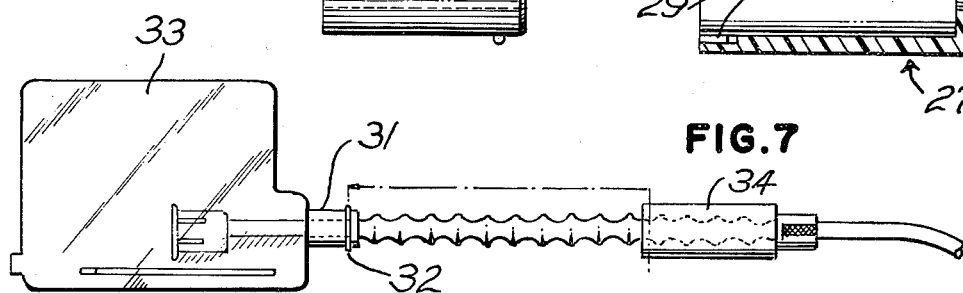

URINE DRAINAGE APPARATUS

This invention relates to urinary drainage apparatus for humans and particularly to equipment in which the tube or conduit leading from the catheter to the urine holding container is collapsible or reducible in length.

There are many persons who are unable to control the drainage of urine from the bladder in a normal manner with the result that elimination presents quite a problem. In some instances there may be an inability to retain the urine in the bladder until a voluntary act of urination occurs and as a consequence undesirable, uncontrollable leakage occurs. In other instances a person may be unable to volitionally urinate due to a blockage or stricture of the urethra or due to an inability to relax the tissues or muscles associated with urination. In these unfortunate medical disorders it is necessary to artificially drain urine from the bladder through a conduit, commonly called a catheter, located in the urethra and opening in the bladder.

The conventional urine drainage apparatus includes such a catheter, a flexible tube or conduit connected at one end to it, and a holding or collecting container at the other end of the tube. The tube is generally four feet, more or less, in length, making it possible for the wearer to move about and turn over in bed. When a person is in bed the container is hung onto the frame at a point lower than the mattress and the tube must be long enough so that it does not pull on the person moving about in bed. However, this long tube gets in the way if the person is walking about or is seated in a chair or wheel-chair. Since the tube is very long and bulky, it can be easily stepped on or pulled out by someone else or the person wearing it, thereby causing painful trauma from the dislodgement and/or the pulling of the catheter from the bladder.

In accordance with the present invention, the tube is collapsible so that it can be shortened in length and means are provided to hold it in its collapsed form. A particular feature of the invention is that the tube itself is continuous in that there are no slippage, telescopic or other joints through which bacteria or other contaminants can enter into the interior of the tube. This is important because, since the catheter remains in the uretha for prolonged periods, it eliminates the rise of infections which could occur if there were an opening between the catheter and the container.

Another feature of the invention is that the collapsible tube readily replaces the conventional tube of urinary drainage apparatus. Thus, a conventional type catheter and a conventional urine holding container may be used with the collapsible tube which is the main feature of this invention. It does not matter whether the catheter has an expansible distal end to serve as a retention bulb or whether it lacks this refinement. It will therefore be apparent that the collapsible tube of this invention may be sold as a separate item for replacement of the simple tube of an ordinary urinary drainage apparatus.

Representative examples of the invention are illustrated in the accompanying drawing in which:

FIG. 1 is a side elevational view of a preferred embodiment of the invention, the collapsible tube being expanded, FIG. 2 is a cross sectional view on the line 2 — 2 of FIG. 1 on an enlarged scale, FIG. 3 is a sectional view on the line 3 — 3 of FIG. 2, FIG. 4 is a sectional view similar to FIG. 3 but showing the tube in a closed or collapsed position, FIGS. 5 and 6 are side elevational views of a modified form of coacting means for holding the tubing in collapsed position, on a slightly smaller scale, a portion of FIG. 6 being broken away, and FIG. 7 is a modification of the assembly of FIG. 1, the coacting holding means being in a reversed relationship from the means in FIG. 1.

Referring first to FIG. 1, the parts as assembled for use include a catheter 10 for insertion in the urethra, a drainage container 11 and a tube 12 connecting them together. The catheter 10 may be a conventional one, with or without an expansible bulbous free end which will serve to retain the catheter with its end in the bladder. The catheter is preferably somewhat flexible but still firm enough so that it may be pushed entirely through the urethra. The tube 12 should be cemented to the catheter or should fit so firmly on it that a leak proof and contamination proof seal is established.

The drainage container 1 may be a conventional urine retaining enclosure and preferably it is a plastic bag so that it is expansible as it fills with urine and will not create a back pressure. The container 11 should have a valved opening through which the container may be periodically emptied but this is not shown as it forms no direct part of the present invention. At the locations where the tube 12 enters the container 11 there should be a leak proof and contamination proof seal, as is established in conventional apparatus. Urine, which enters the catheter 10, flows through it and through the tube 12 into the holding container 11 and there is no place along this entire flow path through which a contaminant may enter.

The entire tube 12, from its attachment to the catheter 10 to its open end within the container 11 is of one-piece, integral construction. The feature of the present invention is that between its ends it is of accordion-like or bellows-like form or construction as is shown at 13. The convolutions in the wall of the tube make it possible to pull the tube out to an expanded, extended or open formation as is shown in FIG. 3 or to push this section of the tube to collapsed, contracted or closed position as is shown in FIG. 4.

The particular formations of the expansible-contractible section 13 are immaterial as variations of this accordion-like construction are well known. Any series of repeating transverse segments along the length of the tube which are flexible enough to permit widening and narrowing of the space between them will serve the purpose. In the drawing, this section 13 is made up of inwardly curved or bowed arcuate portions 14 which are joined at their outer meeting edges at 15, and it is apparent that the inwardly bowed portions 14 could as well be reversed to be outwardly bowed portions, thus locating the sealed edges 15 inwardly of the tube.

Or, the wall of the tube at its expansible-contractible section could be of generally sinusoidal shape in lengthwise cross-section. Other possible variations would have the shape of the tube in patent 3,572,393 to G. A. Eisert, or patent 3,894,540 to F. J. Bonner, Jr., or patent 2,852,216 to M. F. Peters. Sidewise or lateral flexibility at the section 13 is important so that the tube at this section can be curved freely.

The invention includes coacting, cooperating means for retaining or locking the expansible section 13 in the collapsed formation of FIG. 4. This includes a cylindrical sleeve 16 which is cemented to or otherwise held against slippage along the tube 12 at one end of the expansible section 13. It also includes a cylindrical housing 17 which is cemented or otherwise held against slippage on the tube 12 at the other end of the expansible section 13. The housing 17 includes a portion 18 which fits the tube as just explained and a portion 19 with an inside size greater than the largest diameter of the expansible section 13 so that this section can freely move back and forth therein.

To hold together the sleeve 16 and the housing 17 when they are pushed together in the position of FIG. 4, the sleeve 16 is formed with an external annular or circumferential ring or bead 21. This ring snaps in the internal, annular groove 22 near the free end of housing 17. To accomodate this insertion and accomplish this locking movement, the internal diameter of the tubular portion 19 must be large enough to receive the sleeve 16. The sleeve 16 and housing 17 are merely pulled apart when it is desired to open the tube to the extended position of FIG. 3.

To make it easy to grasp the sleeve 16 and housing 17 and exert the locking and unlocking movements, the sleeve is formed with an external frictional surface 23 and the housing is formed with a frictional surface 24. They serve to overcome slippage in the fingers as the parts will generally be made of rubber or a plastic substance having a smooth surface.

The interior of the housing 17 must be long enough to receive all of the expansible section 13 to be collapsed in it. The face 25 of the sleeve 16 could be hollowed out to accomodate some of the collapsible section 13 if this is considered important. It is not necessary that the tubing portion be a solid wall as it does not hold any fluid and this wall may have holes through it which do not interfere with the snap connection.

A variation of the snap connection provided by the ring 21 and the groove 22 is shown in FIGS. 5 and 6. The sleeve 26 of FIG. 5 replaces sleeve 16 and the housing of FIG. 6 replaces housing 17. Instead of the snap ring 21, there are radial pins 28 on the sleeve 26 at its end toward the housing 27. Instead of the internal groove 22, there are bayonet formation grooves 29 on the interior wall of the tubular portion of housing 27. A secure lock is formed between sleeve 26 and the housing 27 when they are pushed together and turned to establish the bayonette interlock.

Another possible variation of the structure is shown in FIG. 7 in that it is a reversed relationship of the arrangement of FIG. 1. The sleeve 31 with its annular ring 32 is located next to the container 33 and may in fact be cemented to it or be made integral with it. The sleeve therefore is a hub-like portion of the container 33 and this eliminates its location along the tube. The housing 34 is the same as housing 17 and it interlocks with the sleeve or hub 31 in the manner shown in FIG. 4. The retaining means of FIGS. 5 and 6 or other coacting, interlocking means may be used in the arrangement of FIG. 7.

Other variations of the invention are apparent. The sleeve 16 can be any member which is held against sliding movement at one end of the section 13 and which has engaging, snapping or hooking means to coact with the housing at the other end of the section 13. The housing can be any member which is held against sliding movement and has a cavity therein to receive the collapsed section 13. The tube 12 could be formed with another section 13 along its length so that the additional foreshortening of the tube is made possible. The section 13 could of course, be cemented into the tube 12 at some point along its length so that an integral-like connection is made.

When the assembly of this invention is used and the tube is in its expanded form the person has the same free movement in bed which is afforded by the usual long tube. When the person is getting out of bed or walking around or sitting in a chair, the tube is considerably shorter and is out of the person's way. It is very unlikely that it will become entangled or stepped on.

What is claimed is:

1. A urinary drainage apparatus which comprises a urinary drainage catheter, a urine holding container, a continuous tube on the order of four feet in length connecting them together and through which urine flows from the catheter directly to and into the container, said tube having a bellows-like section which is expansible so the tube will be long and permit the wearer to move about without dislodging the catheter and is collapsible so the tube will be short and relatively free of entanglement if the person's movement is restricted, and coacting means which engage the tube at the ends of said section and which can be brought together in an interlocking relationship to retain said section in collapsed formation.

2. The apparatus of claim 1, in which said coacting means includes a sleeve at one end of said section and a housing at the other end of the section into which said section can collapse, said sleeve and said housing having engaging means to retain the sleeve and housing together and thereby hold the section in collapsed formation.

3. The apparatus of claim 2 in which said engaging means is an annular ring on the exterior of the sleeve and an annular groove on the interior of the housing.

4. The apparatus of claim 2 in which said engaging means is constituted by a bayonet connection between the sleeve and the housing.

* * * * *